United States Patent [19]

Goshiki

[11] Patent Number: 5,085,863
[45] Date of Patent: Feb. 4, 1992

[54] TUBE PROVIDED WITH A WHITE BISMUTH SALT CONTAINING BISMUTH COMPOUND MIXTURE AS X-RAY OPAQUE AGENT

[75] Inventor: Keigo Goshiki, Saitama, Japan

[73] Assignee: Junkosha Co., Ltd., Tokyo, Japan

[21] Appl. No.: 510,073

[22] Filed: Apr. 17, 1990

[30] Foreign Application Priority Data

Apr. 21, 1989 [JP] Japan ................... 1-103065

[51] Int. Cl.$^5$ ................ A61M 25/00; A61M 5/178
[52] U.S. Cl. ................................. 424/423; 424/4; 424/653; 524/408; 524/430; 524/434; 524/545; 524/546; 524/590; 604/280
[58] Field of Search ................ 424/423, 78, 83, 422, 424/653, 4; 524/408, 430, 434; 604/280

[56] References Cited

U.S. PATENT DOCUMENTS

| | | | |
|---|---|---|---|
| 4,196,731 | 4/1980 | Laurin et al. | 604/280 |
| 4,657,024 | 4/1987 | Coneys | 604/280 |
| 4,838,879 | 6/1989 | Tanabe et al. | 604/280 |

*Primary Examiner*—Thurman K. Page
*Assistant Examiner*—Edward J. Webman
*Attorney, Agent, or Firm*—McGlew & Tuttle

[57] ABSTRACT

A tube comprises a wall formed from thermoplastic material. The wall is provided with an X-ray opaque agent comprised of a white bismuth compound mixture of bismuth oxide and a white bismuth salt such as bismuth nitrate and bismuth sulfate, the bismuth compound mixture having a bismuth content of 83 to 88% by weight.

14 Claims, No Drawings

TUBE PROVIDED WITH A WHITE BISMUTH SALT CONTAINING BISMUTH COMPOUND MIXTURE AS X-RAY OPAQUE AGENT

BACKGROUND OF THE INVENTION

1. Field of the Invention

The present invention relates to a tube which contains an X-ray opaque agent in its wall and is suitable for use as, for example, an indwelling syringe, or catheter.

2. Prior Art

There is known a tube formed from a polymer material having good compatibility with a living organism, such as a fluororesin, and containing an X-ray opaque agent, such as barium sulfate or, bismuth oxide. It is used as, for example, an indwelling syringe which is inserted in a blood vessel fixedly for the transfusion of fluids or blood. This type of syringe has the advantage that, even if an inadvertently broken part thereof may enter the vascular system in the body, it is easy to locate the part by an X-ray photograph, as it contains the X-ray opaque agent in its wall.

It is also used as a catheter which is inserted into the body of a patient for such purposes as the sampling of blood from his heart and the measurement of his blood pressure, while it is observed by fluoroscopy. Specific examples of the known tubes containing the X-ray opaque agents include one containing an X-ray opaque agent distributed uniformly through its entire wall (Japanese Patent Publication No 49394/1972), one having a wall of the triple-layered construction defined by an inner and an outer resin layer not containing any X-ray opaque agent and a middle resin layer existing between the inner and outer layers and containing an X-ray opaque agent(Japanese Patent Application laid open under No.119263/1981), and one having a wall which contains an X-ray opaque agent only in a portion when viewed circumferentially, but along its whole length, i.e., in the form of a strip of a certain width running along the length of the tube (Japanese Utility Model Application laid open under No. 108389/1976).

DRAWBACKS O THE PRIOR ART

Barium sulfate and bismuth compounds are usually employed as the X-ray opaque agent in these tubes. The bismuth compounds exhibit a higher opaque effect than barium sulfate does, and is beneficial for use when it is necessary to obtain a high opaque effect by using a small amount of x-ray opaque agent. However, the bismuth oxide having a higher bismuth content and showing a higher opaque effect than any other bismuth compound has a yellow color and is more difficult to use than white bismuth oxide. For example, it is often the case that doctors or patients are physiologically disposed to prefer a white tube, and that no bismuth oxide giving a yellow color to a tube can be used. Tubes of a material containing bismuth oxide have also the drawback of being difficult to make in any color other than yellow, when tubes having different colors for identification are required.

Bismuth subcarbonate and bismuth oxychloride are bismuth compounds having a white color. They, however, have a lower bismuth content and therefore a lower opaque effect than bismuth oxide. Moreover, they are decomposed at a high temperature and cannot, therefore, be used with, for example, a fluororesin which requires a high temperature for molding.

It is, therefore, an object of the present invention to overcome the drawbacks of the prior art as hereinabove pointed out and provide a tube of a material containing a bismuth-based X-ray opaque agent having a white color and exhibiting a high opaque effect.

SUMMARY OF THE INVENTION

The object of the present invention as hereinabove stated is attained by a tube containing an X-ray opaque agent in its wall formed from a thermoplastic resin, characterized in that the X-ray opaque agent is a white bismuth compound mixture having a bismuth content of 83 to 88% by weight.

OPERATION

According to the present invention, a bismuth compound having a bismuth content of 83 to 88% by weight is used as the opaque agent. Bismuth oxide of high purity having a bismuth content of 89% by weight or above has a yellow color. If, for example, bismuth nitrate or sulfate is mixed with such bismuth oxide, or if they are crystallized together, it is possible to obtain a white bismuth compound mixture. No compound having a bismuth content exceeding 88% by weight is, however, suitable for the purpose of the present invention, as it has a yellow color, while no compound having a bismuth content which is lower than 83% by weight is desirable, either, as it exhibits only a low opaque effect and also lowers the extrusion moldability of a tube. The use of a compound mixture having a bismuth content of 84 to 86% by weight is particularly desirable for the purpose of the present invention.

Although no definite reason is known for the low moldability of a tube from a material containing a bismuth compound mixture having a bismuth content lower than 83% by weight, it is probably due to some change that occurs to the chemical or physical condition of the surfaces of the particles of the bismuth compound.

There is no particular limitation to the thermoplastic resin which can be used for the purpose of the present invention. It is possible to use any known resin that is used for making tubes for medical use. The use of a fluorine-containing resin is, however, particularly effective.

DETAILED DESCRIPTION OF THE PREFERRED EMBODIMENT

The present invention will now be described more specifically with reference to several examples, though the following description is not intended for limiting the scope of the present invention.

In Examples 1 to 3 of the present invention and Comparative Examples 1 and 2, the mixture of bismuth compounds obtained by crystallizing bismuth oxide, bismuth nitrate and bismuth sulfate together, and having the bismuth contents shown in a table below were used as X-ray opaque agents, while the opaque agent employed in Comparative Example 3 consisted solely of bismuth subcarbonate and had a bismuth content of 80.5% by weight. In each Example or Comparative Example, 15 parts by weight of the opaque agent and 85 parts by weight of an ethylene-tetrafluoroethylene copolymer resin (ETFE) were fully kneaded and the mixture thereof was extrusion-molded into a tube. The tubes which had been obtained were compared with one another with respect to their color and moldability. Examination was made of the surface roughness of each tube as a measure of moldability. In the table, each circle marks a tube having a normal surface, and each x a tube having a rough surface.

|  | Example | | | Comparative Example | | |
|---|---|---|---|---|---|---|
|  | 1 | 2 | 3 | 1 | 2 | 3 |
| Bismuth content (%) | 83 | 85 | 88 | 82 | 89 | 80.5 |
| Color | White | White | White | White | Yellow | White |
| Moldability | O | O | O | X | O | X* |

*Unmoldable due to heavy foaming

As is obvious from the results shown above, white tubes could be produced with good moldability from the materials containing the mxiture of bismuth compounds prepared by adding white bismuth compounds to bismuth oxide, and having bismuth contents of 83 to 88% by weight. Therefore, the X-ray opaque agents according to the present invention are comparable to ones comprising barium compounds, and have an advantage over the conventional opaque agents comprising bismuth compounds, as they exhibit a higher opaque effect.

Attempts were also made to use as tube materials other fluororesins, such as tetrafluoroethylene-hexafluoropropylene copolymer, tetrafluoroethylene-perfluoroalkyl vinyl ether copolymer, tetrafluoroethylene, and vinylidene fluoride resins. All of the attempts gave good results.

Not only fluororesins, but also other thermoplastic resins, such as polyurethanes, can be used for the purpose of the present invention. The use of a resin which can be molded into a tube at a lower temperature than when a fluororesin is employed, makes it possible to use in the mxiture of bismuth compounds a white bismuth compound mixture having a lower degree of heat resistance than bismuth nitrate or sulfate, for example, bismuth subcarbonate or oxychloride.

The proportion of the opaque agent which is added to the resin depends on the purpose for which the tube will be used, the mixture of bismuth compounds uses as the opaque agent, etc., but is usually in the range of 3 to 25% by weight of the resin.

The opaque agent may be treated with a surface treating agent, such as a coupling, or surface active agent, before it is mixed with the resin. This treatment improves the distribution of the agent in the resin, the rate at which the mixture thereof can be extruded, etc. It is possible to add a pigment, too, if desired.

ADVANTAGES O THE INVENTION

As is obvious from the foregoing description, the present invention provides a white tube having a high opaque effect and a good molded surface condition, as it employs a white bismuth compound mixture having a bismuth content of 83 to 88% by weight as the X-ray opaque agent.

Although all of the examples which have been described are directed to the case in which the X-ray opaque agent is uniformly distributed throughout the wall of the tube, variations or modifications are, of course, possible within the spirit of the present invention. Possible variations include a tube having a longitudinal wall portion or portions containing the opaque agent, and a tube of the triple-layered wall construction containing the opaque agent embedded between the inner and outer wall surfaces, as hereinbefore described with reference to the prior art.

What is claimed is:

1. A tube comprising a wall formed from thermoplastic material, at least a portion of the wall comprising a resin and agent mixture of a thermoplastic resin and an X-ray opaque agent, the X-ray opaque agent being present in an amount of about 3 to 25% by weight and comprising a white bismuth compound mxiture of bismuth oxide and white bismuth salts, said bismuth compound mxiture having a bismuth content of 83 to 88% by weight, said resin being selected from the group consisting of fluororesins and polyurethanes.

2. Tube of claim 2 wherein the wall is comprised of said resin and agent mixture such that said opaque agent is distributed throughout the wall of the tube.

3. Tube of claim 2 wherein the tube has been formed by molding a mixture of said resin and said opaque agent to form the wall.

4. Tube of claim 1 wherein the bismuth compound mixture has a bismuth content of 84 to 86% by weight.

5. Tube of claim 1 wherein the bismuth compound mixture is a mixture of bismuth oxide and bismuth nitrate.

6. Tube of claim 1 wherein the bismuth compound mixture is a mixture of bismuth oxide and bismuth sulfate.

7. Tube of claim 1 wherein the bismuth compound mixture is a mixture of bismuth oxide, bismuth nitrate and bismuth sulfate.

8. Tube of claim 1 wherein the bismuth compound mixture is a mixture of bismuth oxide and bismuth subcarbonate.

9. Tube of claim 1 wherein the bismuth compound mixture is a mixture of bismuth oxide and bismuth oxychloride.

10. A tube comprising a wall formed from thermoplastic material, at lest a portion o the wall comprising a resin and agent mixture of a thermoplastic resin selected from h group consisting of fluororesins and polyurethanes, and an X-ray opaque agent, the X-ray opaque agent being present in an amount of about 3 to 25% by weight and comprising a white bismuth compound mixture of bismuth oxide and at least one bismuth salt selected from the group consisting o bismuth nitrate, bismuth sulfate, bismuth subcarbonate and bismuth oxychloride, said bismuth compound mxiture having a bismuth conent of 83 to 88% by weight.

11. Tube of claim 10 wherein the wall is comprised of said resin and agent mixture such that said opaque agent is distributed throughout the wall of the tube.

12. Tube of claim 10 wherein the bismuth compound mixture has a bismuth content of 84 to 86% by weight.

13. A tube comprising a wall formed from thermoplastic material, at least a portion of the wall comprising a resin and agent mixture of a thermoplastic resin selected from the group consisting of fluororesins and polyurethanes, and an X-ray opaque agent, the X-ray opaque agent being present in an amount of about 3 to 25% by weight and consisting essentially of a white bismuth compound mixture of bismuth oxide, bismuth nitrate and bismuth sulfate, said bismuth compound mixture having a bismuth content of 83 to 88% by weight.

14. Tube of claim 13 wherein the bismuth compound mixture has a bismuth content of 84 to 86% by weight.

* * * * *